United States Patent
Suissa et al.

(10) Patent No.: US 7,070,488 B2
(45) Date of Patent: Jul. 4, 2006

(54) MICRO-ABRASION DEVICE

(75) Inventors: Michael Suissa, Paris (FR); Sylvain Gleyal, Bretenoux (FR)

(73) Assignee: Bionoface, Paris (FR)

( * ) Notice: Subject to any disclaimer, the term of this patent is extended or adjusted under 35 U.S.C. 154(b) by 0 days.

(21) Appl. No.: 10/531,997

(22) PCT Filed: Oct. 21, 2003

(86) PCT No.: PCT/FR03/03125

§ 371 (c)(1),
(2), (4) Date: Jun. 28, 2005

(87) PCT Pub. No.: WO2004/037098

PCT Pub. Date: May 6, 2004

(65) Prior Publication Data

US 2005/0245180 A1    Nov. 3, 2005

(30) Foreign Application Priority Data

Oct. 21, 2002 (FR) .................................. 02 13077
Oct. 21, 2002 (FR) .................................. 02 13078
Oct. 21, 2002 (FR) .................................. 02 13079

(51) Int. Cl.
*B24C 9/00* (2006.01)

(52) U.S. Cl. ..................... 451/87; 451/90; 451/102; 606/131; 604/289

(58) Field of Classification Search ........ 451/36, 451/38, 39, 87, 90, 102, 60; 606/131, 132; 604/289, 290
See application file for complete search history.

(56) References Cited

U.S. PATENT DOCUMENTS

| | | | |
|---|---|---|---|
| 4,395,850 A | 8/1983 | Brown | |
| 5,207,234 A | 5/1993 | Rosso | |
| 5,810,842 A | 9/1998 | Di Fiore et al. | |
| 6,250,996 B1 | 6/2001 | Metcalf et al. | |
| 6,409,736 B1 | 6/2002 | Bernabei | |
| 6,432,114 B1 | 8/2002 | Rosso | |
| 6,503,256 B1* | 1/2003 | Parkin et al. | 606/131 |
| 6,514,262 B1* | 2/2003 | Di Fiore et al. | 606/131 |
| 6,540,757 B1* | 4/2003 | Hruska et al. | 606/131 |
| 6,562,050 B1* | 5/2003 | Owen | 606/131 |
| 6,641,591 B1* | 11/2003 | Shadduck | 606/131 |
| 6,673,082 B1* | 1/2004 | Mallett et al. | 606/131 |
| 6,726,693 B1* | 4/2004 | Weber et al. | 606/131 |

FOREIGN PATENT DOCUMENTS

| | | |
|---|---|---|
| EP | 0 318 042 B1 | 5/1989 |
| EP | 0 324 448 B1 | 7/1989 |

(Continued)

*Primary Examiner*—Eileen P. Morgan
(74) *Attorney, Agent, or Firm*—Oliff & Berridge PLC

(57) ABSTRACT

The present invention relates to a micro-abrasion device comprising:
  a first reservoir intended to contain a powder to be sprayed onto a surface that is to be treated,
  a second reservoir intended to collect the used powder,
  a handpiece designed to be applied against the surface that is to be treated.

This device comprises a removable cartridge (5) that can be fitted onto the device and removed independently of the handpiece and comprising the first and the second reservoirs.

21 Claims, 12 Drawing Sheets

FOREIGN PATENT DOCUMENTS

| | | |
|---|---|---|
| EP | 0 564 392 A2 | 10/1993 |
| EP | 0 806 184 A1 | 11/1997 |
| FR | 2 712 172 | 5/1995 |
| IT | 1184922 | 10/1987 |
| WO | WO 93/11908 | 6/1993 |
| WO | WO 97/00050 | 1/1997 |
| WO | WO 97/11650 | 4/1997 |
| WO | WO 99/23951 | 5/1999 |
| WO | WO 00/49953 | 8/2000 |
| WO | WO 00/67692 | 11/2000 |
| WO | WO 01/28429 A1 | 4/2001 |
| WO | WO 01/41651 A2 | 6/2001 |

* cited by examiner

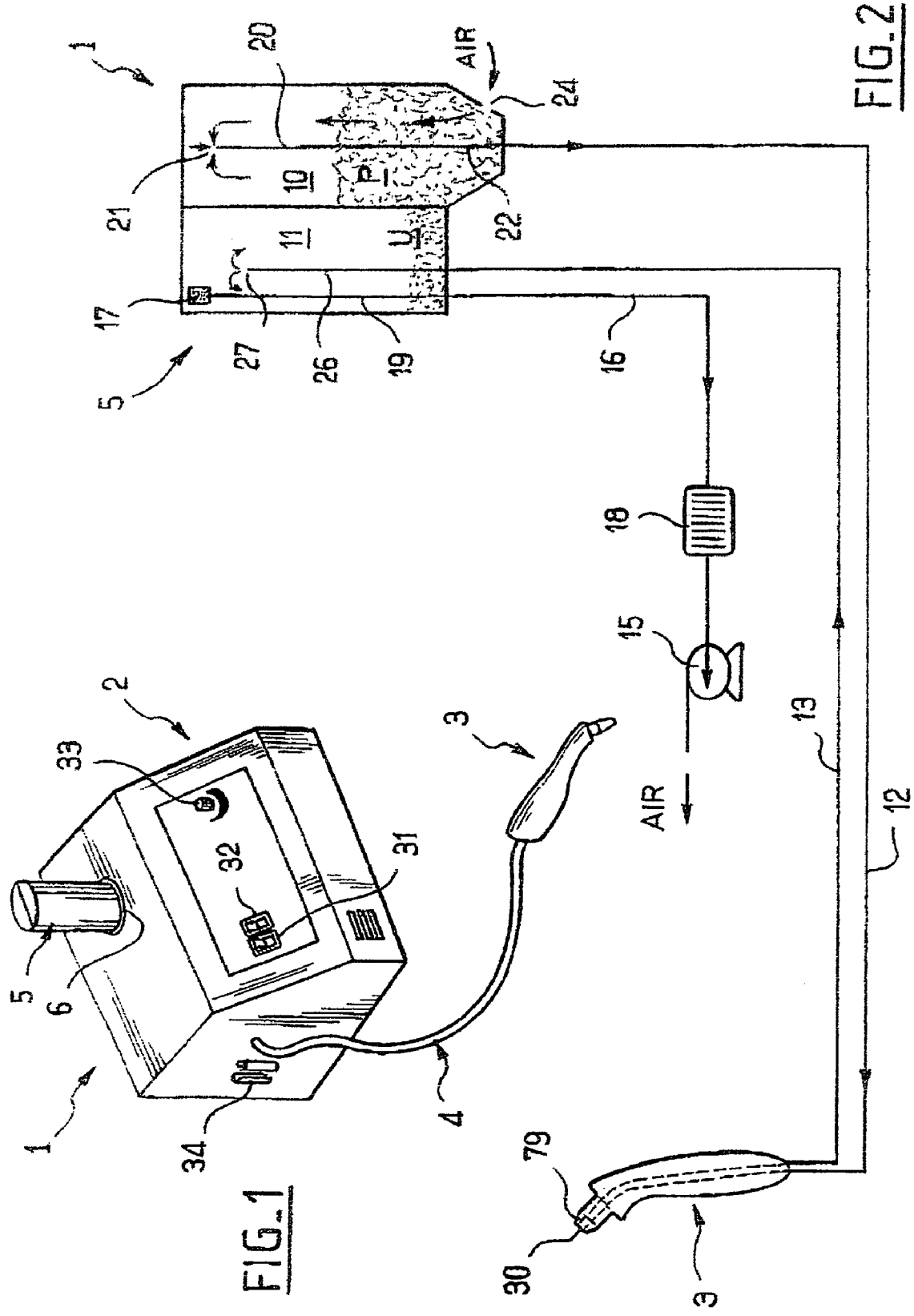

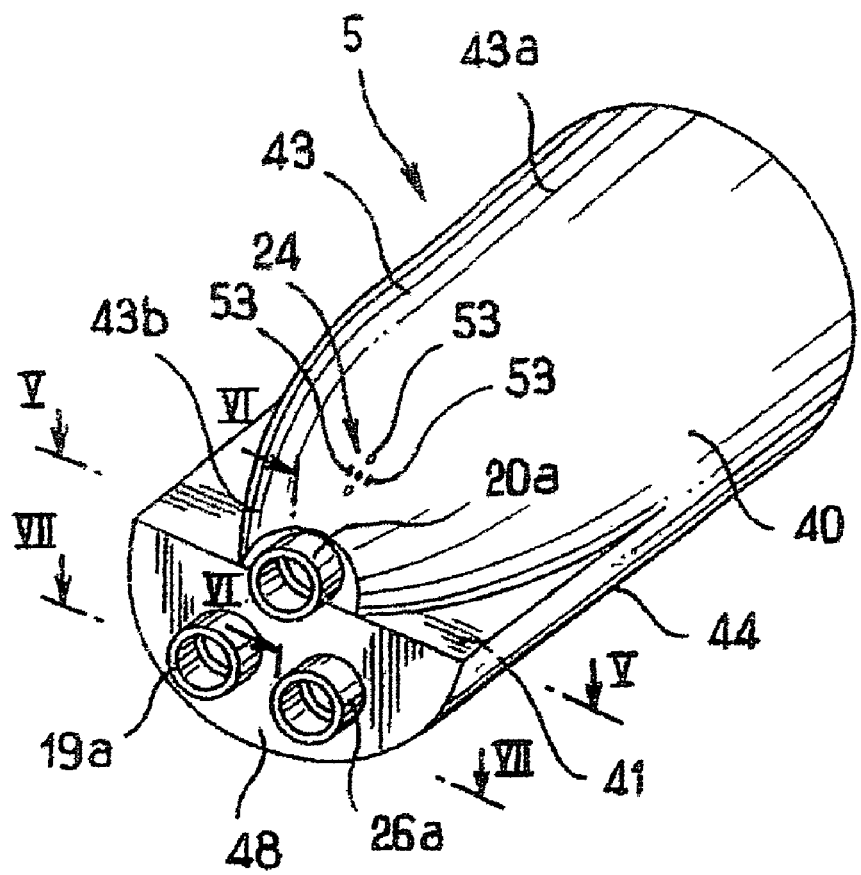
FIG_3
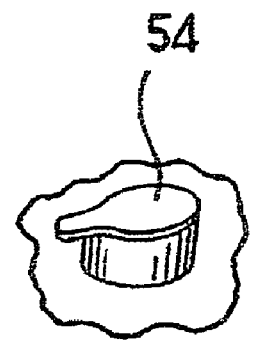
FIG_4

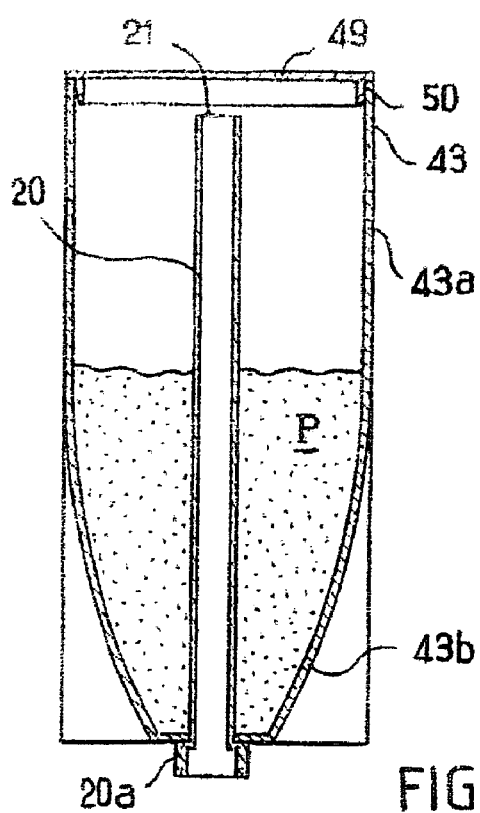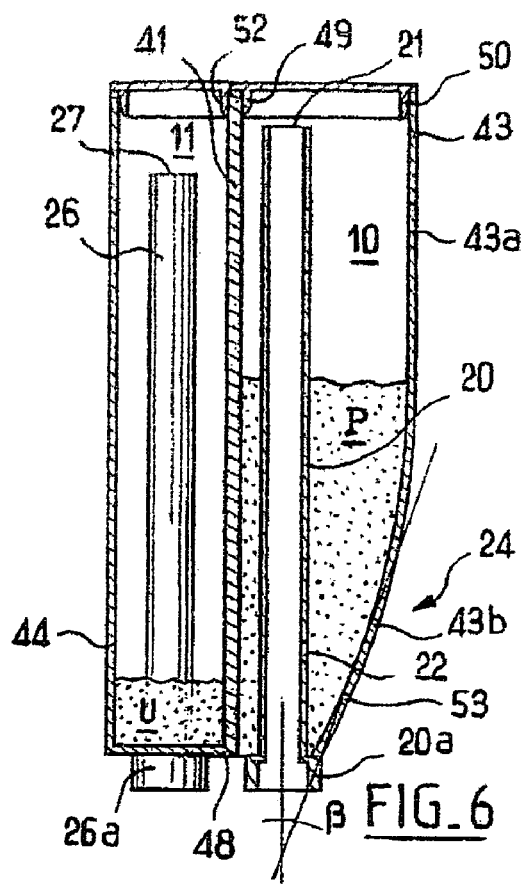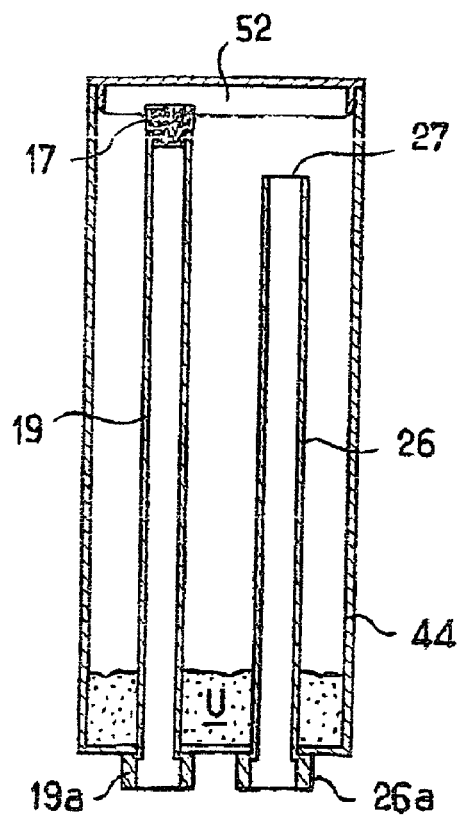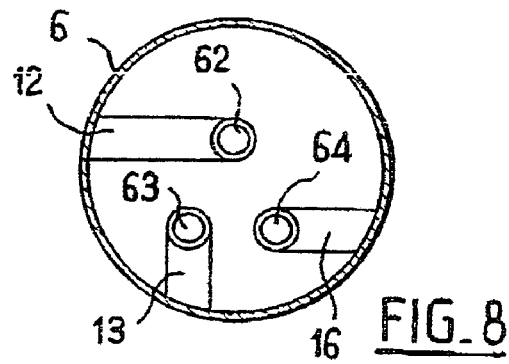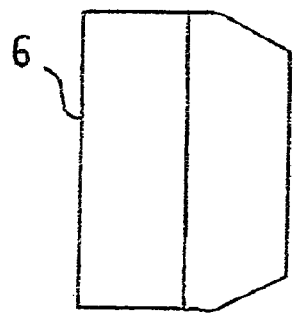

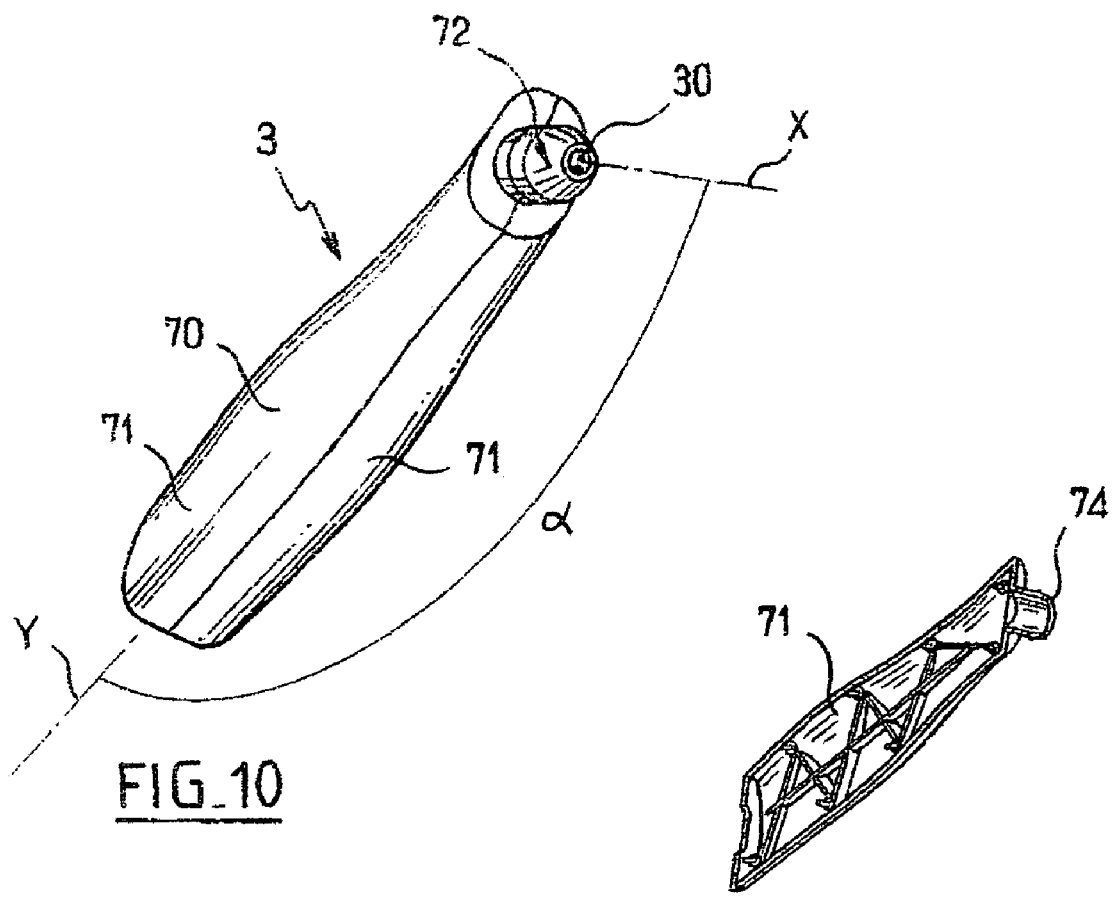
FIG.10
FIG.11
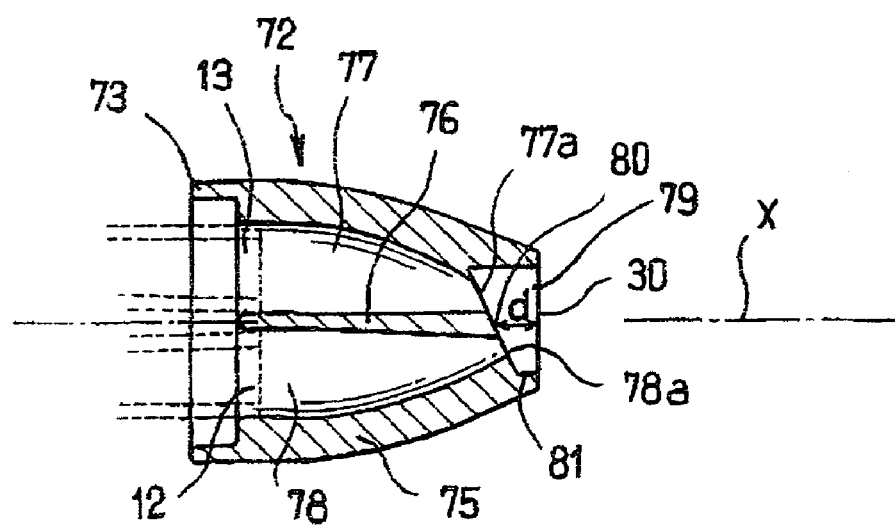
FIG.12

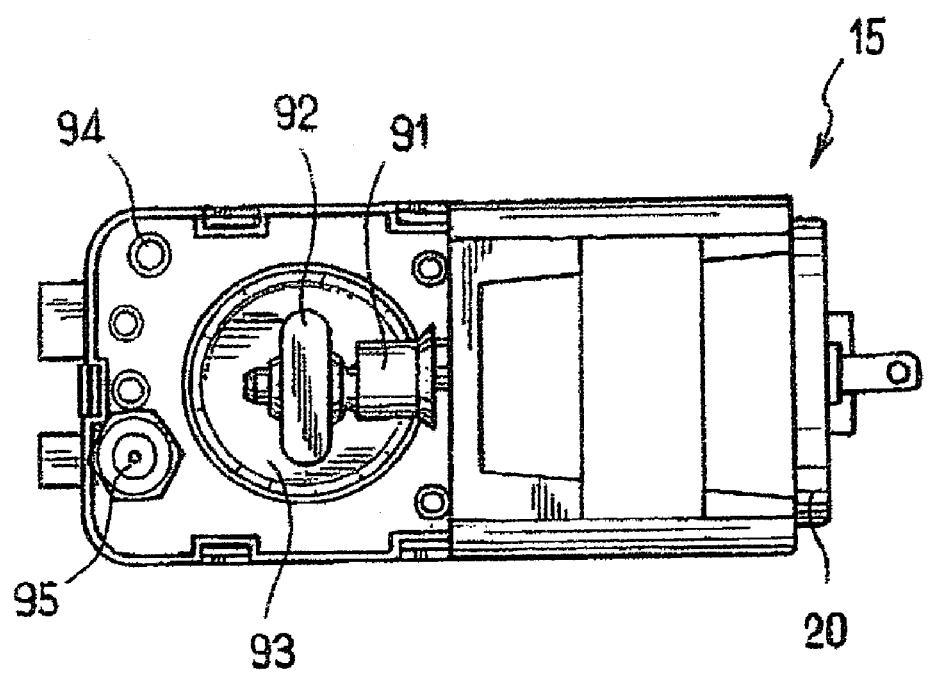
FIG_13
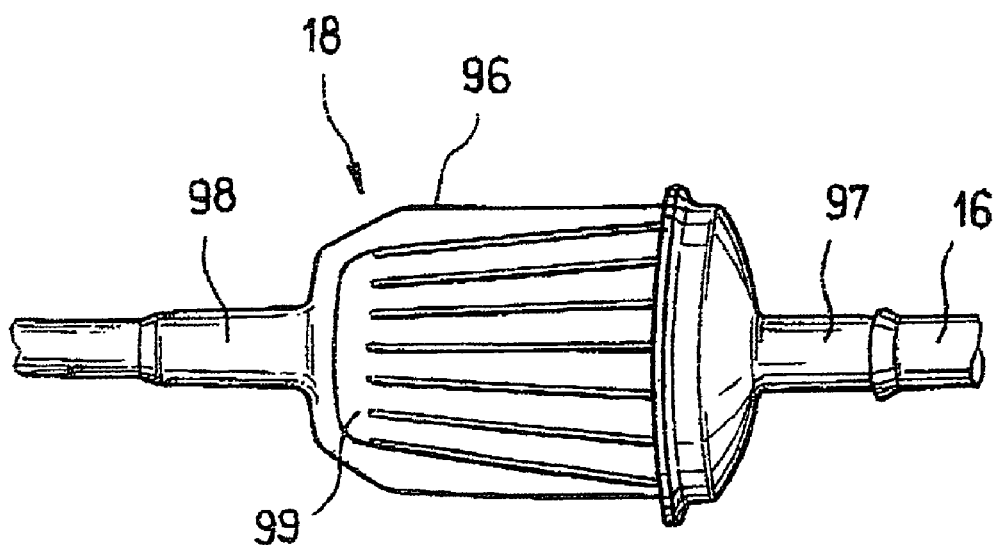
FIG_14

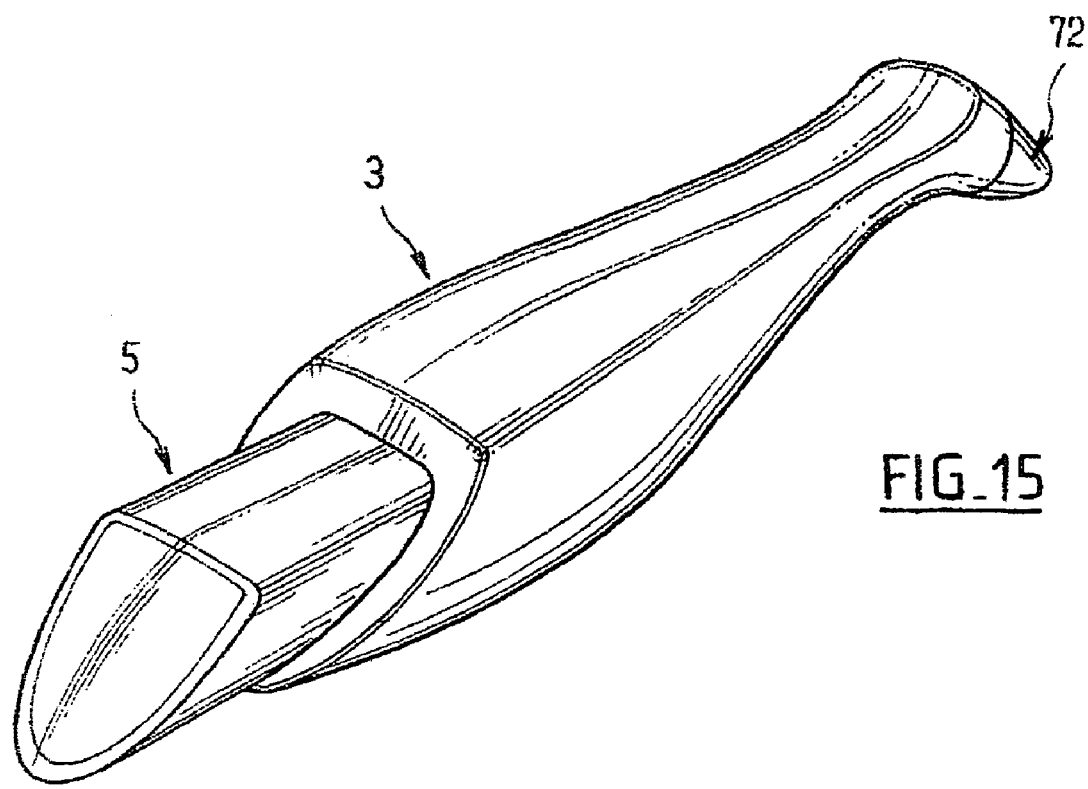
FIG_15
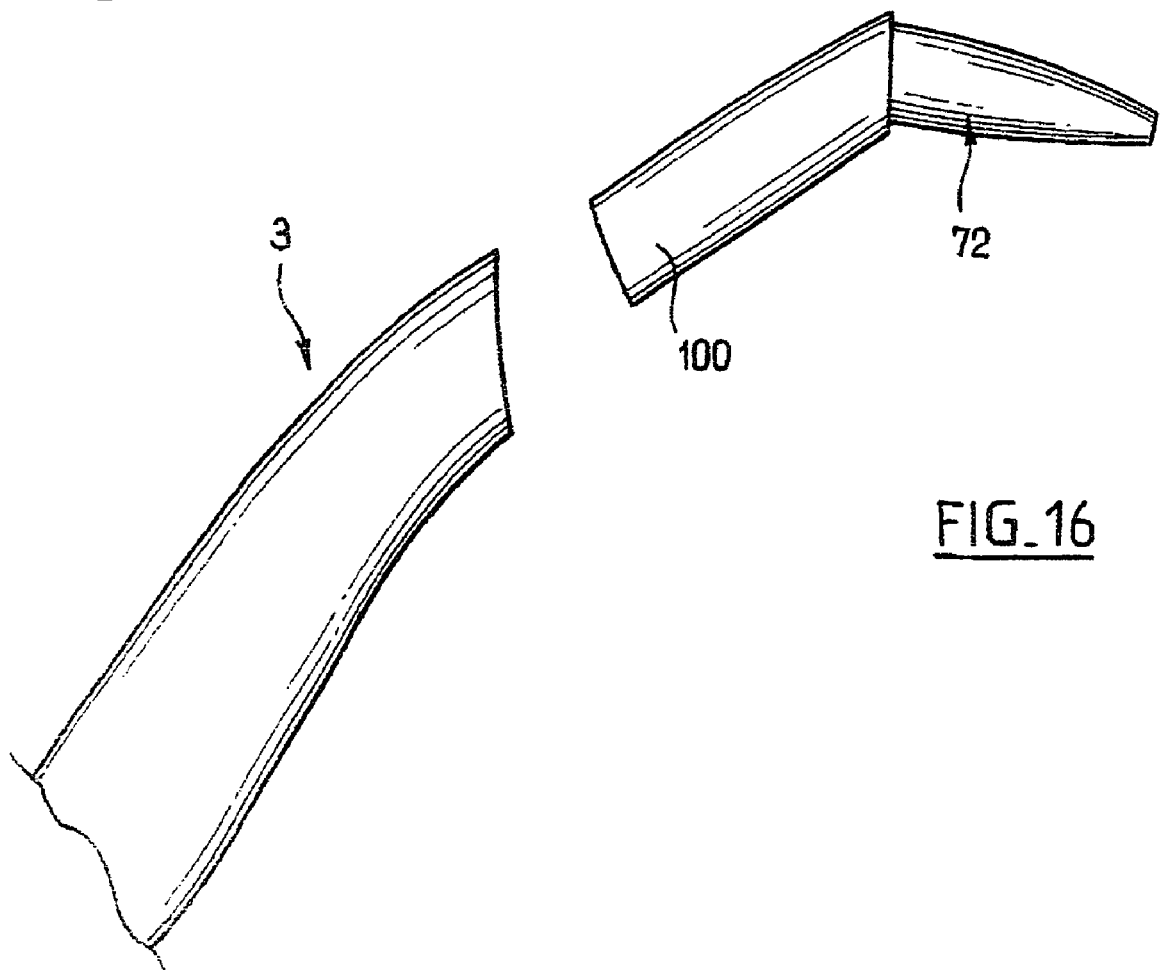
FIG_16

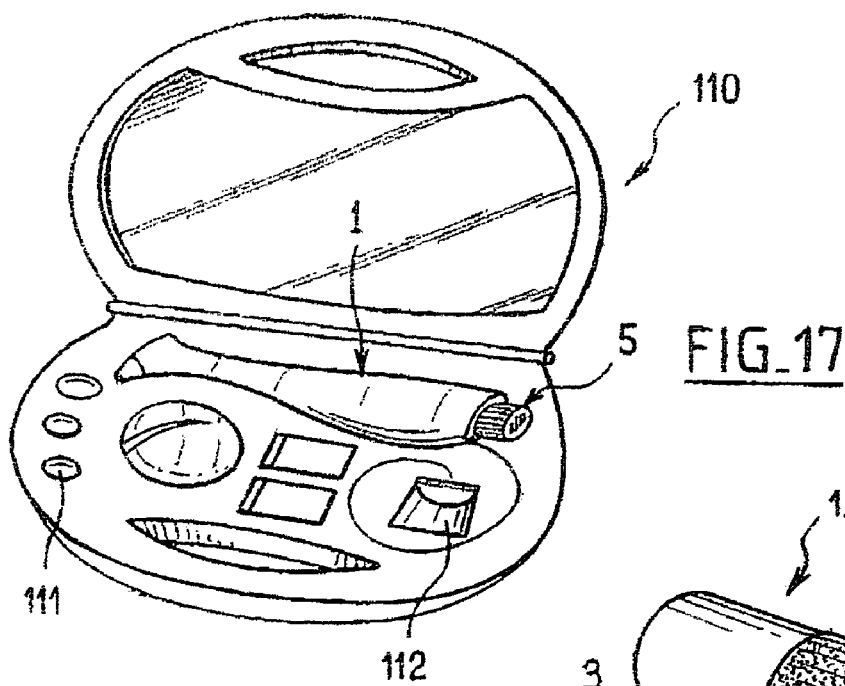
FIG_17
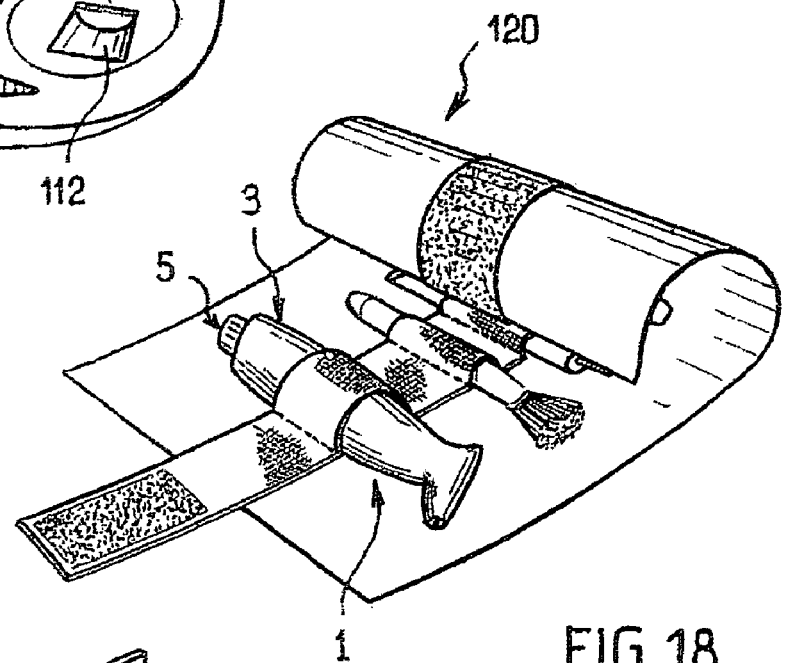
FIG_18
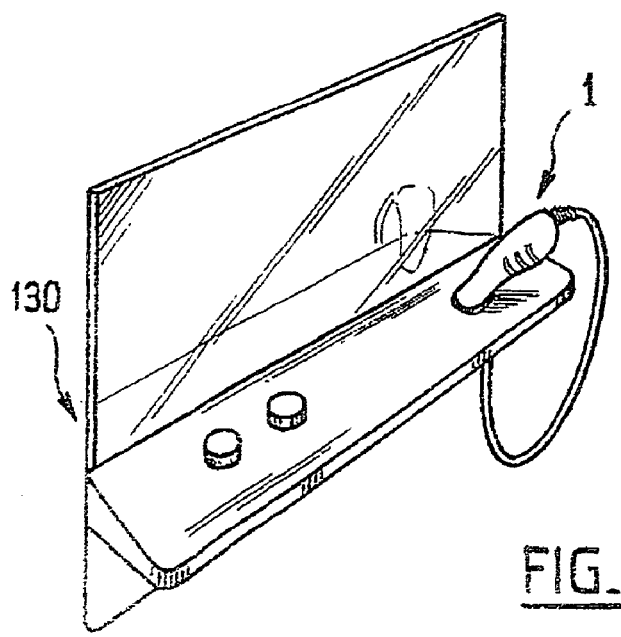
FIG_19

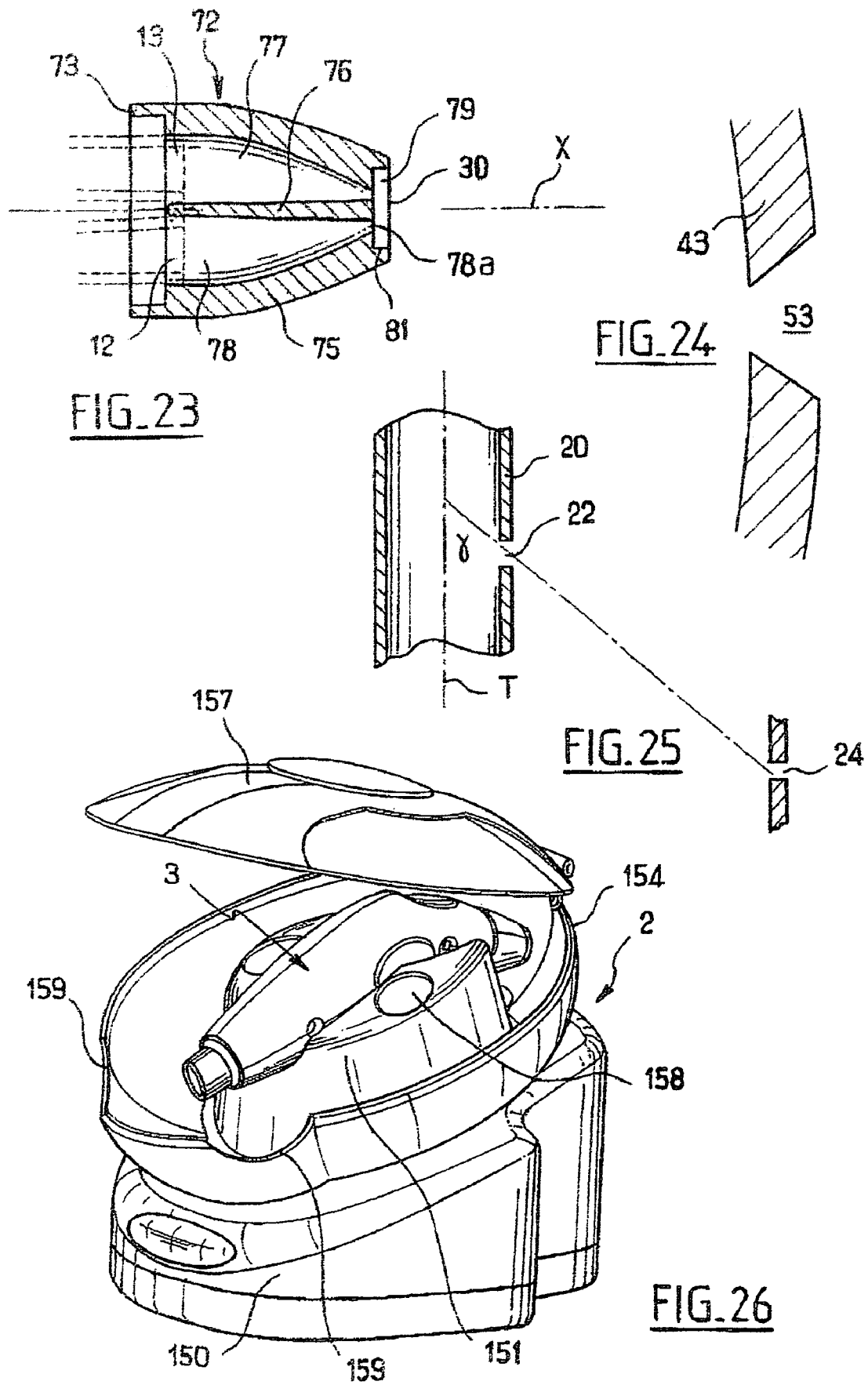

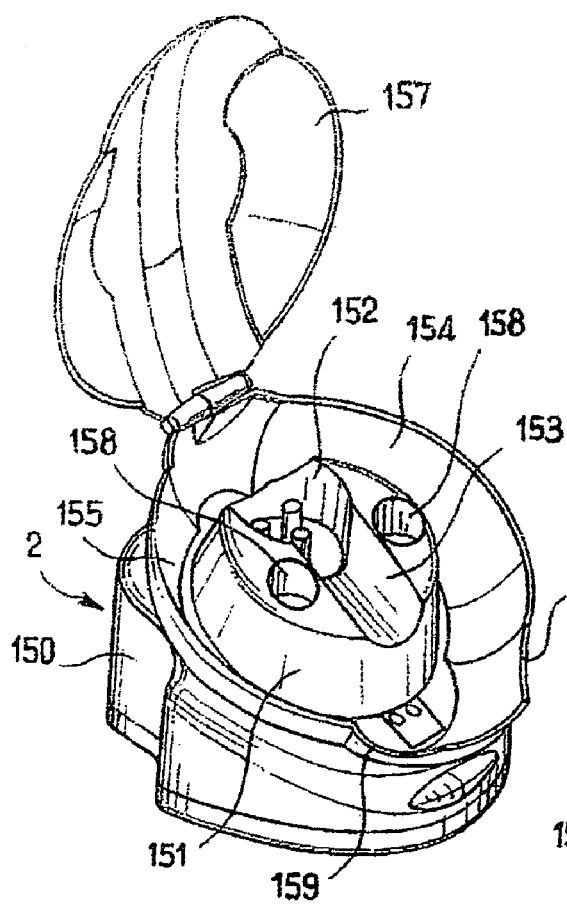
FIG._27
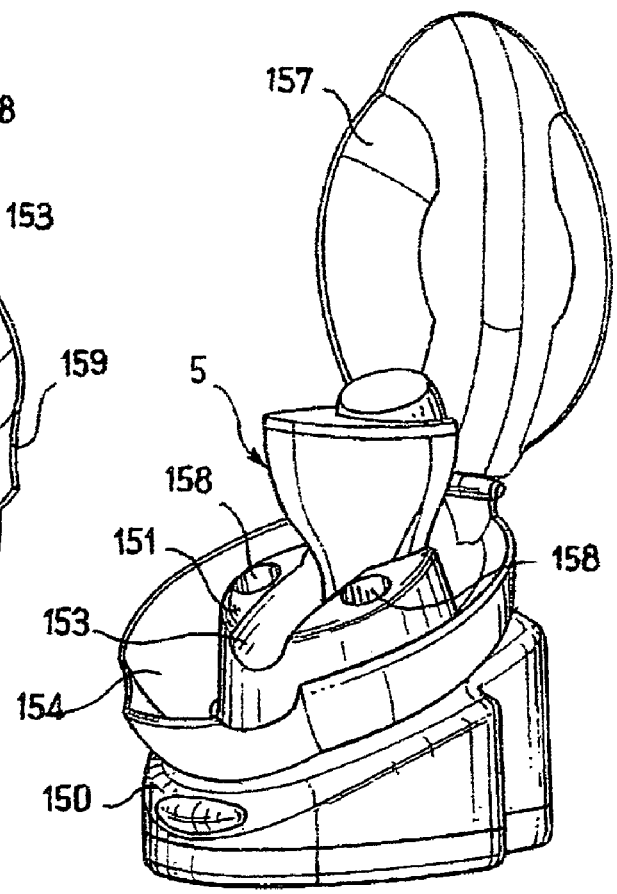
FIG._28
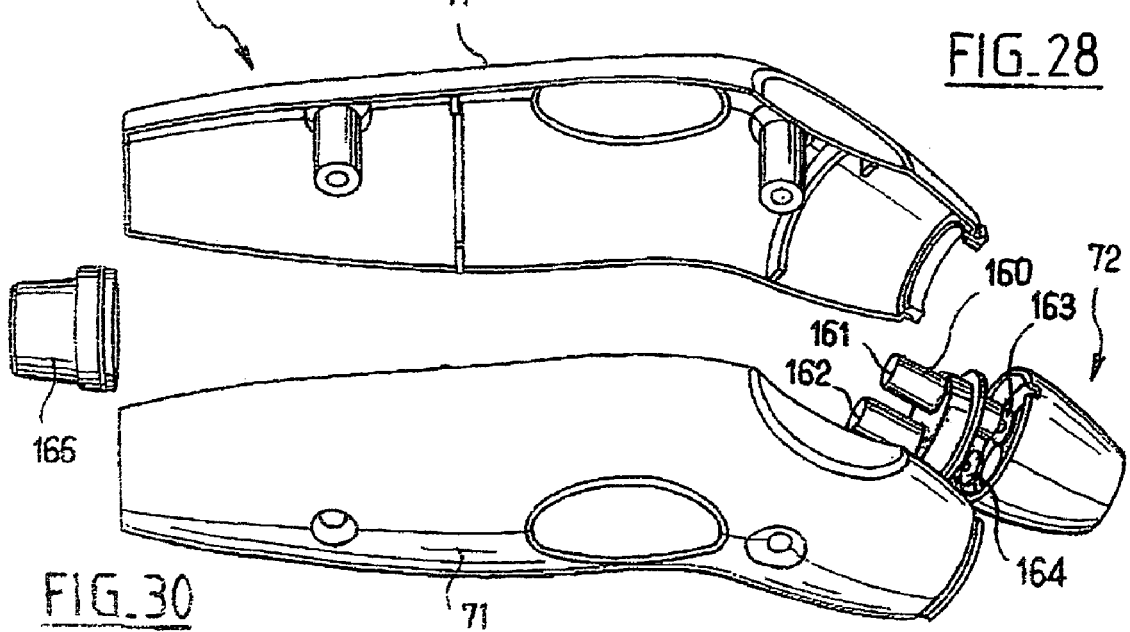
FIG._30

MICRO-ABRASION DEVICE

BACKGROUND

The present invention relates to micro-abrasion devices which work by spraying onto the skin abrasive particles carried by a stream of air.

These devices are widely used in beauty parlours to lessen defects in the skin and/or perform exfoliation treatments.

Micro-abrasion devices which comprise two reservoirs, one containing the unused powder and the other intended to receive the powder after it has been sprayed onto the support that is to be treated, are known. These two reservoirs are made up of independent jars each fitted with a lid that can easily be removed so as to allow the used powder to be removed and the device to be supplied with new powder.

SUMMARY

There is, in particular, a need to make it easier to introduce new powder and remove the used powder.

There is also a need to lower the cost price of the micro-abrasion devices so as to allow them to be offered to the general public.

There is also a need to prevent the re-use of used powder, as this would not be desirable for hygienic reasons.

In one of its aspects the invention aims, amongst other things, to meet all or some of the aforementioned needs.

It achieves this by virtue of a micro-abrasion device comprising:
- a first reservoir intended to contain a powder to be sprayed onto a surface that is to be treated,
- a second reservoir intended to collect the used powder,
- a handpiece designed to be applied against the surface that is to be treated, this device being able to be characterized in that it comprises a removable cartridge that can be fitted onto the device and removed therefrom independently of the handpiece and comprising the first and the second reservoirs.

Thus, a used cartridge can easily be replaced by a new cartridge before a new treatment is carried out.

The first and second reservoirs may be connected together non-removably within the cartridge. In particular, the first and second reservoirs may form two compartments within a body of the cartridge.

The first and the second reservoirs may be contiguous within the cartridge, or arranged otherwise.

The first and second reservoirs may have a common wall, which may make it possible to simplify the manufacture of the cartridge.

The first reservoir may have a section transverse to the longitudinal axis of the reservoir which narrows downwards, which may make it possible to reduce the amount of powder left in the reservoir when the latter is considered to be empty.

The first reservoir may comprise a withdrawing tube, which may be open at its upper end and comprise a lateral orifice allowing the powder to enter the tube.

The withdrawing tube may be entirely secured to the associated reservoir. The tube may for example extend over practically the entire height of the reservoir, it being possible for the open end to be situated a short distance from the top wall of the reservoir.

The device may also comprise a withdrawing tube which has an upper part secured to the reservoir and a lower part, comprising the withdrawing orifice, that can be detached from the reservoir. This lower part may for example consist of an endpiece of the base station, designed to enter the reservoir when the latter is in place.

The cartridge may comprise a coupling sleeve for connecting the withdrawing tube to the base station, this sleeve being able to slide, being capable of moving between a first position in which it closes off an opening in the cartridge, so as to prevent the powder from flowing out, and a second position in which it collaborates with the base station, being, for example, designed to collaborate by fitting-together with an endpiece of the base station. The cartridge may comprise an elastic return member, as appropriate, for returning the sleeve to the first position.

The cartridge may comprise a coupling sleeve for connecting the withdrawing tube to the base station, it being possible for this sleeve to be fixed to a part of the withdrawing tube secured to the body of the cartridge and to make the connection between the withdrawing tube and a cartridge connection opening situated at its base.

The first reservoir may comprise a withdrawing tube made of two parts, namely a first part made as a single piece with one wall of the reservoir, by moulding a plastic, and a second part, mobile or otherwise, attached to the first, comprising the orifice that allows the powder to enter the tube.

As appropriate, at least one of the two parts may be made with a slot and may collaborate with the other part so as to offer a possibility of adjusting the relative position of the two parts. This may make it possible to cause one of the parts to conceal the slot to a greater or lesser extent and therefore alter the cross section of the orifice that allows the powder to enter the withdrawing tube.

The cartridge may have a lid provided with two endpieces, of which the one associated with the first reservoir is used for filling the latter.

The cartridge may comprise a shut-off means for shutting off a connection endpiece for connecting the first reservoir to a withdrawing pipe for withdrawing the powder contained therein.

The device may comprise a base station configured to accept the cartridge. This base station may be provided with a polarizing means preventing the cartridge from being inserted in anything other than in a determined position.

As an alternative, the handpiece may be designed to accept the cartridge.

The cartridge may for example comprise female endpieces communicating respectively with tubes extending inside the first and second reservoirs, these female endpieces being configured to fit onto corresponding male endpieces belonging to the device in a more or less sealed manner when the cartridge is in place on the device.

The device, particularly the base station or the cartridge or both, may comprise a sealing piece made of elastomer. Such a piece can be inserted at least partially between the cartridge and the rest of the device when the cartridge is in the position of use, on the base station for example.

This piece may be made of a silicone polymer, for example. It may have openings allowing the passage of endpieces serving to connect the cartridge, particularly to the base station. It may also comprise at least one lip or annular groove intended to allow sealed connection, this sealing relief being able, for example, to press in a sealed manner against an endpiece belonging to the cartridge.

In order to guarantee the sealing function regardless of the degree of wear of this component, the latter may be configured in such a way as to be able to changed and replaced by a new component. In order to allow a more ergonomic replacement operation, this component may be equipped with a tab or alternatively with a protrusion or with a hollow, which allow the user's hand to gain a better grip on the component.

The latter may also be made within the mass of the cartridge or of the base station using a two-shot injection moulding method, for example.

The cartridge may comprise a body made by moulding a plastic and a closure cap attached to the body.

In another of its aspects, another subject of the invention is a cartridge that can be used in a device as defined hereinabove, comprising a first reservoir containing a powder to be sprayed onto a surface that is to be treated, and a second reservoir intended to receive the used powder.

A further subject of the invention, independent of the foregoing, is a cartridge for a micro-abrasion device, which comprises a reservoir containing the powder to be sprayed onto the skin, this reservoir having a section transverse to the longitudinal axis of the reservoir which narrows downwards.

A further subject of the invention, independent of the foregoing, is a micro-abrasion device which comprises a reservoir intended to receive a powder to be sprayed onto a surface that is to be treated, a withdrawing tube inside this reservoir, this withdrawing tube being provided with at least one orifice for withdrawing the powder, this device being able to be characterized, according to one aspect of the invention, in that the reservoir comprises, on a side wall, an air intake which is arranged in such a way that the air entering the reservoir thereby tends to oppose the clogging of the withdrawing orifice with powder.

A further subject of the invention, independent of the foregoing, is a micro-abrasion device which comprises a reservoir intended to receive a powder to be sprayed onto a surface that is to be treated, a withdrawing tube in this reservoir, this withdrawing tube being provided with at least one orifice for withdrawing powder, this device being able to be characterized, according to one aspect of the invention, in that the reservoir comprises a bottom wall, an inclined wall and an air intake, particularly on the inclined wall and/or on the bottom wall, which is arranged in such a way that the air entering the reservoir thereby tends to oppose the clogging of the withdrawing orifice with powder.

The air intake allows the powder to be stirred up by the air near the edge of the withdrawing orifice, and this reduces the risk of clogging.

That also makes it possible to improve reliability, reduce the cost of the device and make it easier for inexperienced people to use.

In one exemplary embodiment of the invention, the air intake is produced near the withdrawing orifice, particularly at a level appreciably lower down than the latter. The withdrawing orifice may open laterally into the reservoir, for example consisting of a drilling, directed radially, in the withdrawing tube.

In one exemplary embodiment of the invention, the air intake comprises at least one orifice produced in the side wall of the reservoir and the cross section of which is small enough to prevent powder from leaving through the orifice. As an alternative or in addition, the air intake may comprise a filter allowing air to pass but preventing powder contained in the reservoir from leaving.

The air intake may, for example, be produced in the form of a plurality of orifices made in the side wall of the reservoir.

The side wall may be made of plastic.

As mentioned above, the reservoir may be produced with an internal section transverse to the longitudinal axis of the reservoir that narrows downwards. This reduction in the cross section may make it possible to reduce the risk of clogging by reducing the distance between the air intake and the withdrawing orifice.

The lower part of the reservoir may be made, for example, at least partially with a wall the interior surface of which is a portion of a quadric, particularly a portion of a cone, of an ellipsoid or of a paraboloid, converging towards the bottom. The lower part of the reservoir may alternatively be defined at least partially by a polyhedral interior surface, converging towards the bottom.

The lower part of the reservoir may have an interior surface the inclination of which, with respect to the longitudinal axis of the reservoir, at least at one point lies between 20° and 45°.

The straight line passing through an air intake orifice and the withdrawing orifice may make an angle, with the longitudinal axis of the withdrawing tube, which lies for example between 35° and 60°, lying for example between about 48° and 51° approximately. Such an angle may encourage a good flow of powder through the pipework, particularly that of the handpiece, also encourage the creation of the powder/air bi-phasic mixture and improve the flow of the heap of powder in the cartridge.

The air intake may comprise one or several orifices, of constant or variable cross section. A variable cross section, particularly one widening towards the outside, for example conical, may make it easier for the orifice to be formed by moulding.

Another object of the invention, independent of the foregoing, is a cartridge for a micro-abrasion device, this cartridge comprising a first reservoir containing a powder to be sprayed onto the skin and a second reservoir for receiving the particles of used powder, the first reservoir comprising a withdrawing tube which is either provided with at least one orifice for withdrawing the powder, or designed to receive an endpiece comprising a withdrawing orifice, the first reservoir comprising an air intake arranged in such a way that the air entering the reservoir thereby tends to oppose the clogging of the withdrawing orifice.

Another object of the invention, independent of the foregoing, is a micro-abrasion device comprising a handpiece, the latter comprising a part for holding and an endpiece comprising, at one longitudinal end, an opening, for example a roughly circular opening, to be applied against the surface that is to be treated, this opening communicating with a chamber into which at least one duct conveying the particles to be sprayed onto the surface to be treated and at least one duct returning the used particles open, the endpiece being produced with a partition separating the outbound and return ducts.

The opening may have a plane situated some distance from the centre of the adjacent end of the partition, the distance being less than or equal to 2.75 mm, particularly close to 2.5 mm.

The partition may be made as a single piece with the endpiece, particularly by moulding plastic.

The outbound duct may converge towards the centre of the opening.

The axis of the opening in the handpiece to be applied against the surface that is to be treated may make a non-zero angle with the longitudinal axis of the part for holding, this angle preferably being between 100° and 150°.

The outbound and return ducts for the particles may open into a chamber set back from the opening that is to be applied against the surface that is to be treated. This chamber may, for example, have a roughly cylindrical shape, particularly a shape that is a cylinder of revolution.

The endpiece of the handpiece may be produced by moulding an elastomer.

The handpiece may comprise a connector to which the powder supply and return pipes and the endpiece are connected.

The handpiece may comprise two shells which, when assembled, form the part for holding.

Each of the shells may be produced with a half neck, the assembling of the shells forming a neck serving as a support for the endpiece or support for the aforementioned connector.

Each shell may be produced with internal stiffening ribs.

The shells may be configured in such a way that, when assembled, they grip the supply and return pipes.

The handpiece may be connected to a base station comprising at least one pump.

The handpiece may, as an alternative, incorporate at least one pump.

The handpiece may be produced with a housing for accepting a cartridge.

The base station may be produced with a central boss in which a housing is produced to accept the cartridge.

This boss may also be produced with a depression intended to accommodate the handpiece.

The housing accommodating the cartridge may lie below the depression intended to accommodate the handpiece so that this housing is covered by the manipulator and thus protected from dirt when the device is not in use.

The base station may comprise an annular housing around the central boss, allowing the hose connecting the handpiece to the base station to be wound around the boss.

This housing may be formed by a bowl fixed to a base of the base station. The latter may comprise a hinged lid allowing the boss and the handpiece in place thereon to be covered when the device is not in use.

The lid may be arranged in such a way that it cannot be closed if the cartridge is in place on the base station.

The base may comprise a bottom plate comprising housings for attaching a pump and a filter in particular.

The base may have two lateral openings so that the handpiece can be rested on the base station without having to reposition it in the depression provided for permanent storage.

BRIEF DESCRIPTION OF THE DRAWINGS

The invention may be better understood from reading the detailed description which will follow, of some nonlimiting exemplary embodiments, and from examining the attached drawing, in which:

FIG. 1 is a schematic perspective view of a micro-abrasion device according to one exemplary embodiment of the invention, FIG. 2 is a functional diagram of the device of FIG. 1, FIG. 3 depicts, in isolation and in perspective, the cartridge used in the device of FIG. 1, FIG. 4 illustrates the closure of an endpiece of the cartridge using an inner seal, FIG. 5 is a schematic longitudinal section on V—V of FIG. 3, FIG. 6 is a schematic longitudinal section on VI—VI of FIG. 3, FIG. 7 is a schematic longitudinal section on VII—VII of FIG. 3, FIG. 8 depicts, schematically and partially, in a view from above, the opening accommodating the cartridge, FIG. 9 depicts, in a view from above and schematically and partially, another example of the shape of an opening for accommodating a cartridge, FIG. 10 is a perspective depiction of the handpiece, FIG. 11 depicts, in isolation, one of the two shells of the handpiece of FIG. 10, FIG. 12 depicts, in isolation and in axial section, schematically, the endpiece of the handpiece of FIG. 10, FIG. 13 depicts, in isolation, viewed from above and schematically, a pump that can be used in the device of FIG. 1, FIG. 14 schematically depicts, in a side view, a filter that can be used in the device of FIG. 1, FIG. 15 depicts, in perspective, schematically, an alternative form of device produced according to the invention, FIG. 16 illustrates the possibility of producing the handpiece with a removable head, FIG. 17 depicts schematically a case comprising a micro-abrasion device according to the invention, FIG. 18 schematically depicts a roll incorporating a micro-abrasion device according to the invention, FIG. 19 schematically depicts a bathroom shelf equipped with a micro-abrasion device according to the invention, FIG. 20 schematically depicts another exemplary embodiment of the invention, FIG. 23 is an axial section, similar to FIG. 12, of an alternative form of embodiment, FIG. 24 depicts, on a larger scale, one of many examples of a cross section of an air intake orifice, FIG. 25 is a partial and schematic axial section aimed at illustrating the relative positioning of the withdrawal orifice and of the air intake, FIG. 26 is a schematic and partial view, in perspective, of an alternative form of micro-abrasion device, FIG. 27 depicts the device of FIG. 26 with the handpiece removed, FIG. 28 depicts the device of FIG. 26 after the cartridge has been fitted, FIG. 30 is a partial and schematic exploded view of the handpiece of the device of FIG. 26, FIG. 31 partially and schematically depicts the cartridge and the part that accepts the cartridge.

DETAILED DESCRIPTION

Figure 20:
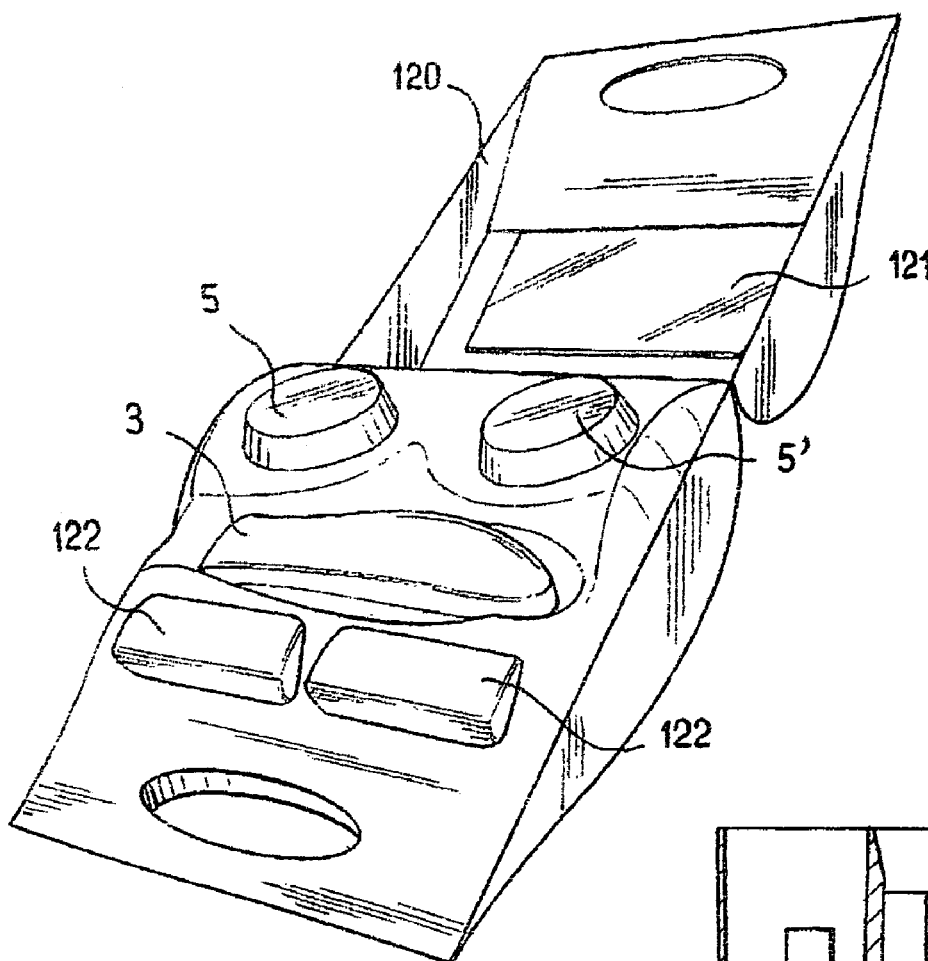

FIG. 1 depicts a micro-abrasion device 1 according to an exemplary embodiment of the invention.

This device 1 comprises, in the example considered, a base station 2 and a handpiece 3 connected to the base station 2 by a hose 4.

The base station 2 is designed to accept a cartridge 5 and comprises an opening 6 for this purpose.

The principle of operation of the device 1 will now be described with reference to FIG. 2, this description being valid also for the other exemplary embodiments described later on.

The cartridge 5 comprises a reservoir 10 containing an unused abrasive powder P, for example between 30 and 70 cm³ of powder, for example of the order of 50 cm³ of powder, and a reservoir 11 to receive the used powder U.

The powder P is conveyed to the handpiece 3 by means of a supply pipe 12 and the used powder U is returned to the reservoir 11 from the handpiece 3 by means of a return pipe 13.

A vacuum pump 15 is connected to a suction pipe 16 which is connected to a suction tube 19 opening into the reservoir 11 through an inlet filter 17. A second filter 18 is placed upstream of the pump 15 to more finely filter the air sucked into the pipe 16. This second filter 18 could, as appropriate, be omitted provided that an adequate inlet filter 17 is used.

A withdrawing tube 20 extends over practically the entire height of the reservoir 10 and has an open upper end 21 and, towards the bottom of the reservoir, a lateral orifice 22 serving to withdraw 22 the powder P. In practice, the lateral orifice may be subdivided as appropriate into several inlets.

An air intake 24 is made in the wall of the reservoir 10, this being arranged in such a way as to reduce the risk of the lateral orifice 22 becoming clogged, as will be specified later on.

The return pipe 13 opens into the reservoir 11 via a return tube 26 having an upper end 27 opening into the upper part of the reservoir 11, at a level preferably below that of the inlet filter 17.

The way in which the device 1 works is as follows.

When the pump 15 is in operation, air is sucked in through the inlet filter 17 and this creates, in the reservoir 11 of used powder U, a pressure drop which causes air to be drawn in through the return pipe 13.

The delivery 12 and return 13 pipes communicate with a chamber 79 of the handpiece 3 which opens to the outside via an opening 30, the latter being closed off in use when the handpiece 3 is pressed against the surface that is to be treated.

When the handpiece 3 is not being used, the opening 30 communicates with the atmosphere and the delivery pipe 12 is at atmospheric pressure, which means that powder P is not withdrawn from the reservoir 10.

When the handpiece 3 is being used, the reduced pressure created by the pump 15 in the reservoir 11 is transmitted via the return pipe 13 to the chamber 79 of the handpiece 3 and this creates a reduced pressure in the supply pipe 12 and air is drawn in through the opening 21 of the withdrawing tube 20. The air sucked out from the reservoir 10 is compensated for by an arrival of air through the air intake 24. The powder P is withdrawn through the withdrawing orifice 22, carried along by the air flowing through the delivery pipe 12 as far as the opening 30 where it sprayed onto the surface that is to be treated. After having bounced off the treated surface, the particles are sucked back into the reservoir 11 through the return pipe 13.

The device 1 has the advantage that the powder P is not sprayed towards the opening 30 unless there is close enough contact between the handpiece 3 and the surface that is to be treated that so the chamber 79 is cut off from the outside and allows a circulation of air between the reservoirs 10 and 11 to be established.

The base station 2 may comprise, as depicted, an on/off switch 31, an indicator lamp 32 indicating operation and, as appropriate, a knob for adjusting the power of the pump 15, this knob for example operating an electronic device allowing the motor of the pump 15 to be run more quickly or more slowly.

The base station 2 may also comprise a support 34 on which the handpiece 3 can be hooked when not in use.

The base station 2 may operate autonomously, on batteries, or with an accumulator battery and, as appropriate, comprise a transformer to allow it to be connected to the mains.

An example of a cartridge 5 will now be described more specifically with reference to FIG. 3 to 7.

In the example considered, the cartridge 5 comprises a body 40 which can be manufactured by moulding plastic, particularly a polyolefin, being made as can be seen in FIG. 6 with a vertical partition 41 defining two compartments within the body 40, these compartments corresponding respectively to the aforementioned reservoirs 10 and 11.

The reservoir 10 is delimited by a part 43 of the body 40 which has a roughly semicylindrical upper portion 43a and a lower portion 43b that narrows towards the bottom. The reservoir 11 is delimited by a part 44 of the body 40 which is more or less semicylindrical over its entire height. The slope β of the lower portion 43b is chosen as a function of the ability of the powder P to flow, particularly as a function of its tendency to stick to the wall of the reservoir 10. The slope β may, for example, particularly at the region of the air intake 24, lie between 20° and 30°.

Figure 21:
FIG. 21 illustrates the production of a tube as one piece with the body of the reservoir.

In the example illustrated, the body 40 is produced with an end wall 48 which comprises three openings for the passage of the tubes 19, 20 and 26 respectively. These tubes are fixed for example by welding, clipping or bonding to the end wall 48 and comprise, at their lower end, respective female endpieces 19a, 20a and 26a which each come to rest against the end wall 48 by means of a shoulder. The tubes could alternatively be produced as one piece with the body of the reservoir, for example by moulding, as illustrated in FIG. 21.

The cartridge 5 comprises a closure cap 49 fixed to the body 40 for example by clipping, welding or bonding.

This cap 49 comprises sealing skirts 50 and 52 allowing the reservoirs 10 and 11 to be sealed more or less hermetically in their upper part.

As a preference, the cartridge 5 is produced in such a way as not to allow an unequipped user to access the content of the reservoirs, so as to prevent the used powder U from being reused.

The amount of powder P contained in the cartridge 5 may be suitable to one single treatment session, for example.

Prior to first use, the endpiece 20a of the withdrawing tube 20 may be closed off as illustrated in FIG. 4 by means of a removable or puncturable inner seal 54 or by any other shut-off means such as a cap for example. A removable inner seal, not depicted, may also be present on the body 40 to close off the air intake 24 and prevent moisture from entering the reservoir 10 prior to first use.

FIGS. 3 and 6 in particular show that the air intake 24 may be produced in the form of at least one orifice 53, particularly a plurality of orifices 53, the cross section of which is chosen to be small enough to prevent particles of powder P from leaving while at the same time allowing air to enter the reservoir 10.

In the example considered, the air intake 24 has several, particularly five, orifices 53, these together offering the air a passage with a cross sectional area that may be between 0.2 and 2 mm² for example, and may particularly be about 1 mm².

The air intake may comprise one or several orifices which, as illustrated in FIG. 24, have a cross section widening towards the outside, changing for example from a diameter of 0.2 mm to a diameter of 0.3 mm. Such a shape may make the orifice easier to produce when moulding the part 43.

The air intake 24 is advantageously situated below the level of the lateral orifice 22 of the withdrawing tube 20, so as to allow, when the device is operating, the air that enters the reservoir 10 through the air intake 24 to stir up the powder upwards in the vicinity of the orifice 22 and reduce the risk of the latter becoming clogged. At least a fraction of the air entering through the air intake 24 may also reach the orifice 22 and make it easier for the particles of powder P to enter the tube 20. The proportion, by volume, of the solid particles in the air sprayed onto the treated surface is, for example, below 10%, or even below 5%, for example close to 3%.

The angle γ formed by the straight line joining the lateral orifice 22 and the air intake 24 with the axis T of the tube 20 is, for example, close to 50°, as can be seen in FIG. 25.

FIG. 8 depicts, in a view from above, the opening 6 in the housing of the base station 2 intended to accept the cartridge 5.

This figure shows that the male endpieces 62, 63 and 64 are present in the end wall of this housing to collaborate respectively, in a more or less sealed fashion, with the female endpieces 20*a*, 26*a* and 19*a* of the cartridge 5, so as to cause the tubes 20, 26 and 19 to communicate with the pipes 12, 13, 16 respectively.

The arrangement of the endpieces 22*a*, 26*a* and 19*a* is advantageously chosen in such a way as to constitute a polarizing means ensuring that the cartridge 5 can be fixed into its housing only in a determined position.

In an alternative form of embodiment of the invention, this polarizing may be obtained not by a special layout of the endpieces 62, 63 and 64 but by giving the opening 6 an outline that does not have axial symmetry, for example with one side truncated as illustrated in FIG. 9, the body 40 of the cartridge 5 having an external cross section of corresponding shape. In FIG. 9, the endpieces 62, 63 and 64 have not been depicted, so as to make the drawing clearer.

The male endpiece 62, intended to fit into the female endpiece 20*a* associated with the reservoir 10, may be configured to pierce the inner seal 54 mentioned above, when the cartridge 5 is fitted into the device 1.

The handpiece 3 will now be described with reference to FIGS. 10 to 12. This handpiece comprises a part 70 for holding, produced by assembling two shells 71, one of which is depicted in isolation in FIG. 11, and an endpiece 72 which is depicted in isolation in FIG. 12, in axial section.

The axis X of the opening 30 makes an angle α of between 100 and 150° with the longitudinal axis Y of the part 70 for holding, and this contributes to the ergonomics of the handpiece 3.

The endpiece 72 comprises a mounting skirt 73 which allows it to be fixed onto a neck 74, of axis X also, formed by the assembly of two halves each produced using a shell 71. The skirt 73 connects to a wall 75 of the endpiece which converges towards the opening 30.

A partition 76 produced as one piece with the rest of the endpiece 72 by moulding plastic separates, within the endpiece 72, return 77 and supply 78 ducts which open out via respective orifices 77*a* and 78*a* into the chamber 79.

The ducts 77 and 78 are arranged, on the opposite side to the orifices 77*a* and 78*a*, to allow the attachment of the flexible pipes of the hose 4, which correspond to the pipes 12 and 13.

The cross section of the ducts 77 and 78 decreases in the direction towards the chamber 79, because of the shape of the wall 75 and also because the partition 76 has a thickness that increases as it nears the chamber 79.

The end wall 80 of the chamber 79, into which wall the orifices 78*a* and 77*a* open, extends obliquely with respect to the axis X, the orifice 77*a* being further away from the opening 30 than the orifice 78*a*, and having a larger cross section.

The chamber 79 has a side wall 81 which, in the example considered, is a cylinder of revolution of axis X.

The cross section of the orifice 78*a*, smaller than that of the orifice 77*a*, allows the particles to be sprayed onto the skin at a relatively high speed; the cross section of the orifice 77*a*, which is wider, facilitates the return of the particles to the return pipe 13. The cross section of the supply duct 78 diminishes, for example between the opening used to attach the flexible pipe and the orifice 78*a*, by a factor of between two and ten within the endpiece, particularly of at least five.

The relative position of the ducts 77 and 78, offset on either side of the axis X of the opening 30, and their orientation towards the centre thereof, makes it easier for the particles to bounce back towards the return duct 77.

An endpiece 72 is thus obtained which can be made at a relatively low cost while at the same time offering good effectiveness, this making it possible for a lower-powered pump 15 to be used if so desired, while at the same time maintaining a satisfactory result.

The distance d between a point situated at the centre of the end of the partition 76 coinciding with the end wall 80 of the chamber 79 and the plane of the opening 30 may for example be less than 2.75 mm, in the example considered being close to 2.5 mm, which allows a relatively large amount of powder to be left on the skin to give the user the ability to see where the handpiece has passed. For a value of 50 $cm^3$ of powder used, more than 5% of the powder may, for example, remain on the skin, the value of used powder U returned to the device being, for example, 47 $cm^3$ when the reservoir of powder P is empty.

FIG. 23 depicts an alternative form of the endpiece 72, in which the chamber 79 has an end wall perpendicular to the axis X.

FIG. 13 depicts, in isolation, an example of a pump 15 that can be used in the device 1.

The pump 15 is, in the example considered, known per se, of the diaphragm type driven by an electric motor 90 connected by an eccentric 91 to a rod 92 secured to the diaphragm 93, the rod 92 being made as a single piece of elastomer with this diaphragm.

The pump 15 comprises an inlet endpiece 94 for connecting the suction pipe 16 and a delivery endpiece equipped with a cross section reducer 95 to reduce the operating noise.

As the electric motor 90 rotates, the rod 92 oscillates in a direction generally perpendicular to the plane of FIG. 13, and this actuates the diaphragm 93.

In the example considered, the pump output is, for example, approximately one liter per minute.

FIG. 14 depicts an example of a filter 18. The latter comprises a casing 96 provided with inlet 97 and outlet 98 endpieces and inside this casing there is a filter bag 99, the wall of which is pleated. The endpiece 97 is connected to the pipe 16 downstream of the filter 18.

Of course, the invention is not restricted to the example which has just been described.

In particular, the micro-abrasion device may be produced as illustrated in FIG. 15 in such a way as to allow the cartridge 5 to be fixed to the handpiece 3, it being possible for the latter to incorporate the pump 15 and the filter 18 and also possibly a power source.

The cartridge 5 may in particular be housed in a housing in the handpiece 3 opening out at the opposite end to the endpiece 72.

It is also possible, as an alternative, to connect the handpiece 3 to a base station 2 comprising the pump 15 and the filter 18 while at the same time allowing the cartridge 5 to be fixed to the handpiece.

It is also possible, as illustrated in FIG. 16, to produce the handpiece 3 in such a way as to allow a removable mounting of the endpiece 72, the latter for example being secured to a connector 100 configured to fit into a housing provided for this purpose in the part for holding. This may make it possible, particularly in the case of use in a beauty parlour, to change the endpiece 72 between clients.

A micro-abrasion device according to the invention may advantageously, as illustrated in FIG. 17, be incorporated in a case 110 comprising cosmetic products 111, for example products for preparing the skin and/or for caring for it after the treatment. In this example, the handpiece accepts the cartridge 5 and incorporates the pump, but is connected to a power source 112, for example a mains adaptor, by an electric lead.

The micro-abrasion device may alternatively form part of a skin care or make-up roll 120, as illustrated in FIG. 18, or be incorporated into a bathroom cabinet or shelf 130, as illustrated in FIG. 19.

The micro-abrasion device may also comprise a base station comprising a hinged lid 120, as illustrated in FIG. 20. This lid may house a mirror 121 for example.

The base station 2 may be arranged to accept the cartridge 5 that is being used and a spare cartridge 5' intended to replace the cartridge 5.

The base station 2 may be designed also to accept containers 122 containing products to be applied to the skin before and/or after treatment.

The powder P may comprise any pulverulent agent capable of producing abrasion and, for example, particles of corundum or powders based on cereal flours. By way of example of powders based on cereal flours, mention may be made of powders exhibiting a glasslike] structure resulting from the polymerization and cross-linking of cereal flours in an alkaline environment using a cross-linking agent chosen from the group formed of formolation agents and maleic anhydride, such powders being described in patent application FR 2 761 365, the content of which is incorporated hereinto by reference.

The powder P may also incorporate at least one cosmetic or care active ingredient.

By way of an active ingredient that can be incorporated into the powder, mention may be made, amongst others, of vitamins, for example vitamin C, skin-protecting agents, antibacterial agents, antiwrinkle agents, hydrating agents, moisturizers, scents, preservatives, sun filters, fatty acids or oils, this list being non-limiting.

The powder may contain particles having a dimension ranging for example between 50 and 180 µm, better between 50 and 160 µm, better still between 80 and 150 µm. The size is given by the statistical particle size distribution at half the population, known as D50.

Use may be made of a pump other than a diaphragm pump. However, the use of a diaphragm pump is preferred when the micro-abrasion device is intended for the general public because such a pump can be manufactured at a cost compatible with large scale distribution.

The cartridge may also be produced differently.

In particular, the cartridge may be produced by assembling two reservoirs joined together by clipping, welding, particularly ultrasound welding, or bonding or by a support member. The two reservoirs may in particular each be produced with a flat wall and be contiguous via these walls.

The two reservoirs may alternatively be manufactured with a common part formed by welding and comprising a film hinge allowing the configuration of this common part to be altered after release from the mould, so as to form the cartridge.

The two reservoirs may be placed side by side or one inside the other.

At least one of the reservoirs may be produced with a transparent window allowing the user to see the level of powder contained within.

The cartridge may be equipped with at least one valve intended to prevent powder from coming out when the cartridge is being handled in order to fit it into or remove it from the device.

Figure 22:
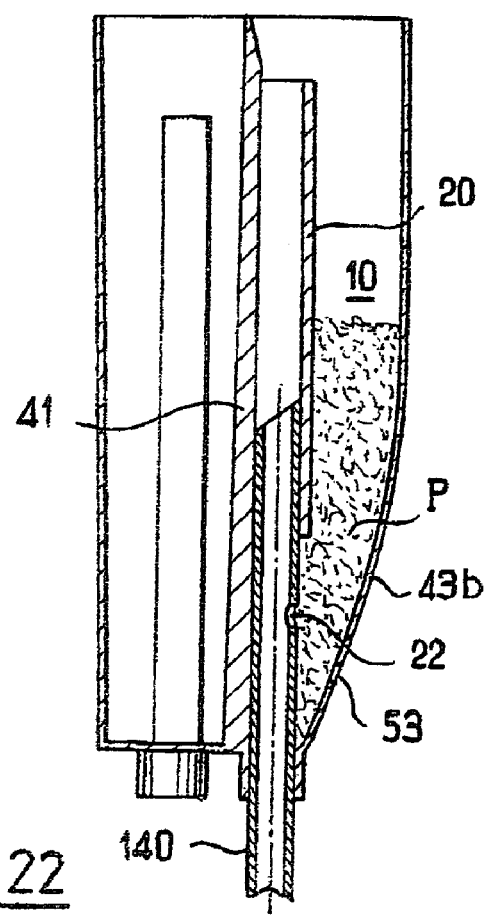
FIG. 22 is a schematic longitudinal section depicting an alternative form of cartridge with a withdrawing endpiece engaged inside the reservoir containing the new powder.

The withdrawing orifice 22 may alternatively be produced on an endpiece 140 intended to penetrate the reservoir 10 containing the powder, as is the case in the alternative form of embodiment illustrated in FIG. 22.

In this embodiment, the withdrawing tube 20 present inside the reservoir 10 is contiguous with the partition 41 and has a lower opening into which the endpiece 140 can fit, this latter endpiece belonging to the base station 2 for example.

Such an arrangement makes it easier to produce the withdrawing tube in a single piece with a wall of the reservoir 10, because the withdrawing orifice 22 is present on the endpiece 140 manufactured separately.

Another embodiment of the invention will now be described with reference to FIGS. 26 to 29.

In this example, the base station 2 comprises a base 150 comprising a boss 151 provided with a housing 152 to accept the cartridge 5. This boss 151 also comprises a depression 153 accepting the handpiece 3 when the device is not in use. The boss also comprises two housings 158 to accommodate two endpieces 72 to be fitted at the end of the body of the handpiece, for example two spare endpieces.

Figure 29:
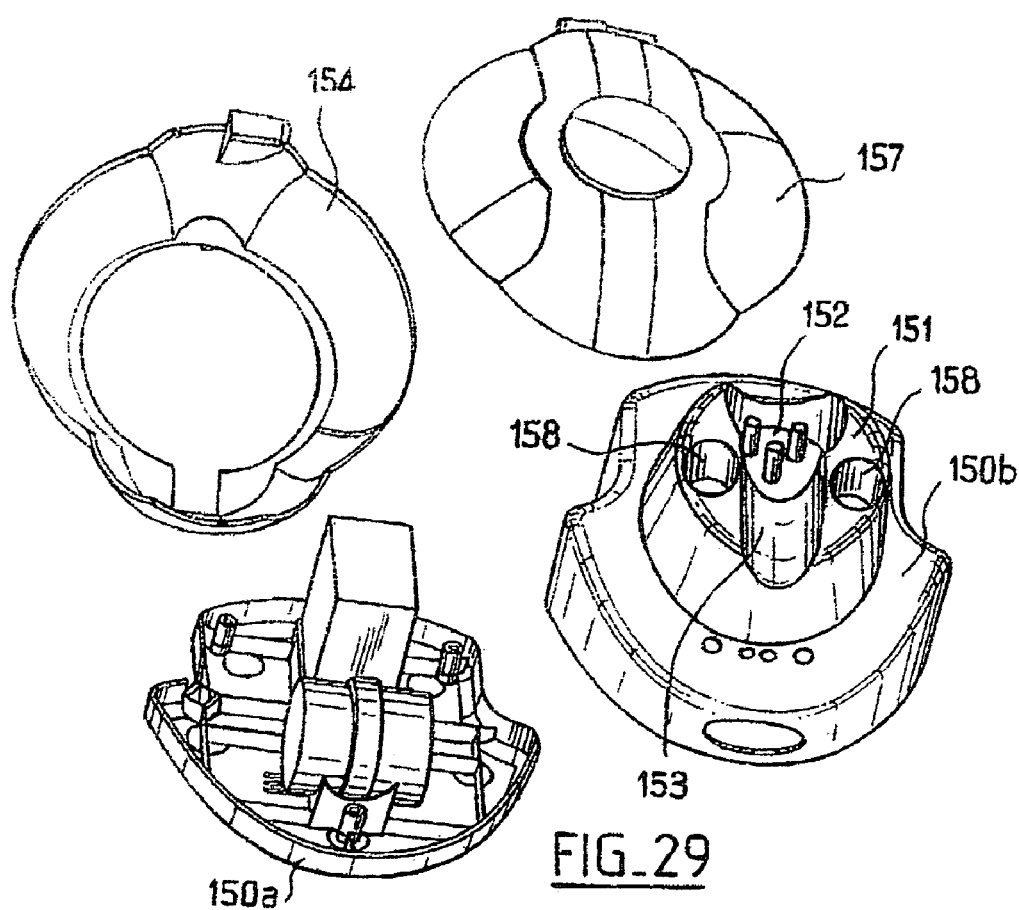
FIG. 29 is an exploded partial view of the base station of the device of FIG. 26.

The base station 2 comprises a bowl 154 which defines around the boss 151 a housing of annular overall shape 155 able to house the hose when the handpiece 3 is in place on the boss 151, this hose not having been depicted in FIG. 26 in order to make the drawing clearer. The front part of the bowl is also equipped with two openings 159, each for example having an outline in the general shape of an arc of a circle for accommodating the handpiece in a transverse position. A lid 157 is hinged to the bowl 154, it being possible for this lid 157 to be folded down onto the handpiece 3 when the latter is in place in the depression 153. The base 150 may consist of the assembly of a bottom plate 150*a* and of a cap 150*b*, as can be seen in FIG. 29, it being possible for the plate 150*a* to be produced by moulding with housings to accommodate a filter and a pump.

The handpiece is depicted in isolation in FIG. 30.

It can be seen that this handpiece comprises a connector 160 which is held by the two shells 71 when these are assembled and which comprises endpieces 161 and 162 for connecting the powder supply and return pipes and two endpieces 163 and 164 communicating with the endpieces 161 and 162 respectively and engaged inside the final endpiece 72. The latter may be produced with a shape that allows it to be clipped onto the connector 160 and/or the shells 71 once these have been assembled. The handpiece may also comprise a grommet 166 allowing the hose that connects it to the base station out.

Figures 31, 32:
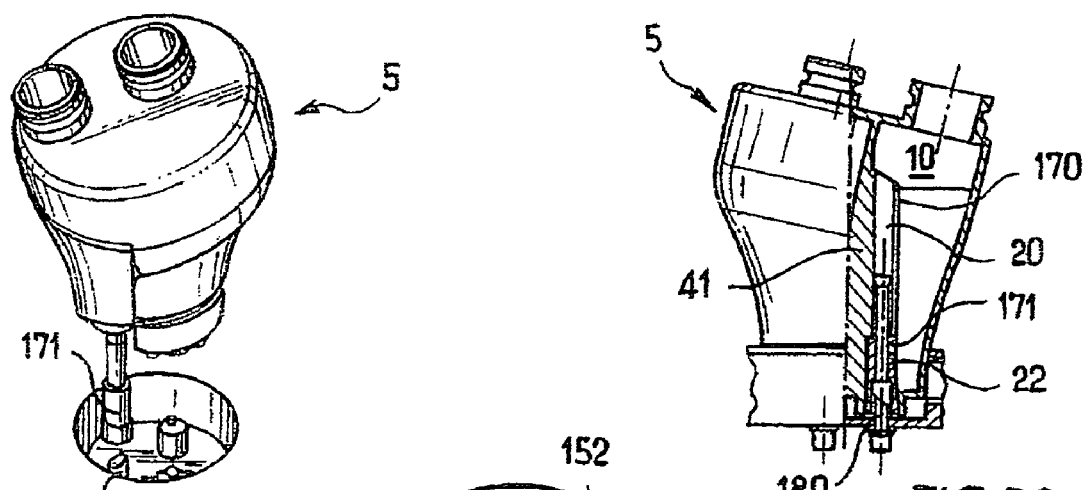
FIG. 32 is a partial and schematic axial section of the cartridge in place in the accepting part.
Figure 33:
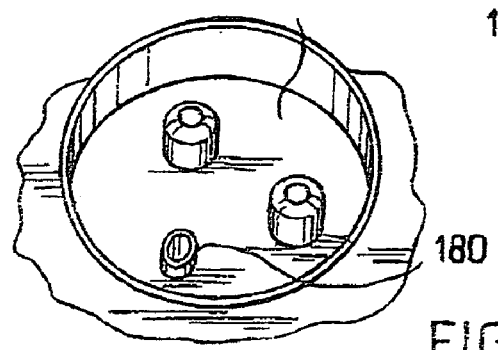
FIG. 33 depicts in isolation, schematically, the accepting part.
Figure 34:
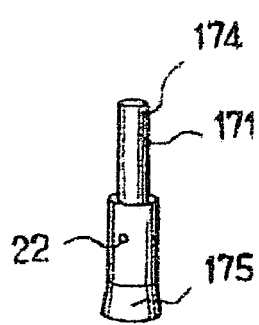
FIG. 34 depicts part of the withdrawing tube which is attached into the cartridge.

If reference is now made to FIGS. 31 and 32 it can be seen that the withdrawing tube 20 may be produced in two parts, namely an upper part 170 made as a single piece by moulding with the partition 41 separating the reservoirs 10 and 11, and a lower part or connecting sleeve 171, attached to the upper part 170, provided with a lateral orifice 22. The sleeve 171 has been depicted in isolation in FIG. 34 and it may be seen that it comprises, at its upper end, an endpiece 174 designed to enter the upper part 170 of the withdrawing tube. The sleeve 171 also has, at its lower end, a widened portion 175 which makes it possible to obtain a seal against the corresponding lower opening of the cartridge 5. It may also be able to act as a stopper in order to prevent the powder from flowing inadvertently when the cartridge is being disconnected. When this cartridge is in place on the base station, an endpiece 180 for withdrawing powder, secured to the base station, enters the sleeve 171. This endpiece 180 may have an end cut at an angle, as can be seen in particular in FIG. 33, so as to tear an inner seal as appropriate, this inner seal being, for example, welded or bonded onto the corresponding opening of the reservoir 10.

The material of which the sleeve 171 is made may be chosen for example in such a way as to encourage the obtaining of a seal on contact with the upper part 170 of the withdrawing tube and with the withdrawing endpiece 180.

Figure 35:
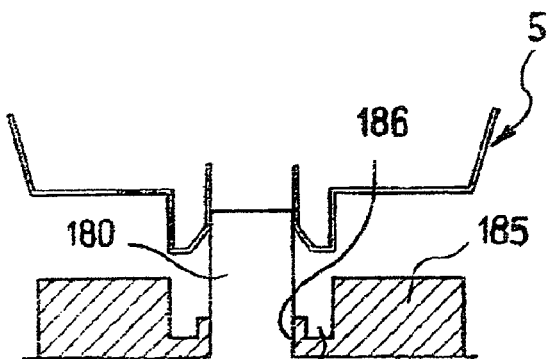
FIG. 35 depicts in schematic and partial axial section, a sealing piece.
Figure 36:
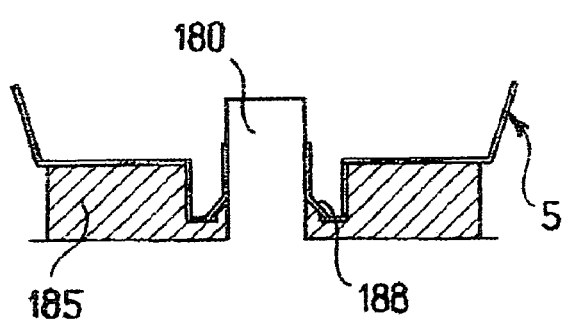
FIG. 36 is a view similar to FIG. 35, after the cartridge has been fitted.

When the cartridge is being manufactured, it may be produced by moulding without the sleeve 171 then the latter may be introduced into the cartridge, the lateral orifice 22 being produced by moulding with the sleeve 171. The bottom of the housing 152 accommodating the cartridge 5 is advantageously provided with a sealing piece 185, not visible in FIGS. 31 and 33 and depicted schematically and partially in FIGS. 35 and 36, for example a disc made of an elastomer such as a silicone polymer, comprising openings 186 for the passage of the various connecting endpieces for connecting the base station 2 to the cartridge 5 and against which the cartridge 5 can press when it is in place on the base station 2.

The cartridge may be designed in such a way as to negotiate, by clip fastening, at least one relief on the base station, so as to compress the sealing piece to a certain extent when in the clipped-in position.

Grooves may for example be provided around the periphery of the cartridge, so as to face complementary protrusions on the base station and fulfill a function of holding the cartridge in position in order thus to make sure that the sealing piece 185 is compressed.

The sealing piece 185 may be produced with a shape that contributes to the obtaining of sealing.

The sealing piece 185 may for example comprise, around each endpiece for connection of the base station to the cartridge, at least one annular groove 187 against which a complementary lip 188 produced on the cartridge 5 can press, so as to obtain a seal that is good enough for the device to work correctly.

The invention is not restricted to one particular way of obtaining a sealed connection.

A removable sealing piece made of elastomer may prove unnecessary and the sealing piece may be fixed permanently for example to the cartridge or the base station.

As appropriate, the cartridge and/or the base station may have an elastomer coating deposited by dipping or spraying or alternatively overmoulded, for example using a two-shot injection moulding technique.

Figure 37:
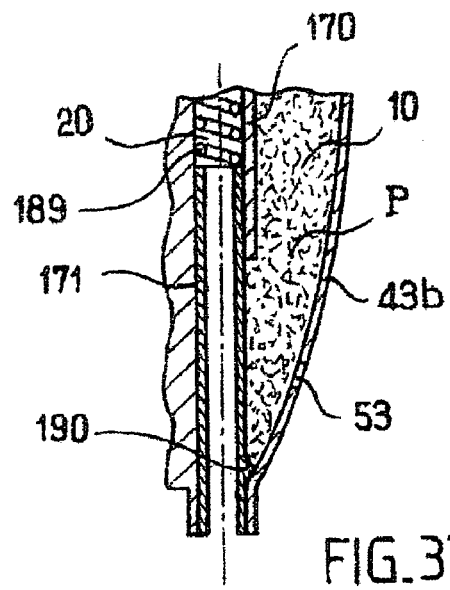
FIGS. 37 to 39 are partial and schematic axial sections depicting details of alternative forms of embodiment.

FIG. 37 illustrates the possibility of producing the cartridge 5 with a coupling sleeve 171 mounted with a possibility of sliding relative to the upper part 170 of the withdrawing tube 20. The sleeve 171 may in particular be able to move between a position depicted in FIG. 37, in which it prevents the powder P from flowing through the lower opening of the reservoir 10 of the cartridge 5 and a retracted position in which the sleeve 171 has slid inside the upper part 170, against the return action of a spring 189 for example. The return of the sleeve 171 occurs when the cartridge is put in place on the base station, the endpiece 180 pushing the sleeve 171 back. This sleeve may be produced with at least one relief such as a tooth 190 capable, by elastic deformation, of negotiating the lower opening of the reservoir 10, while at the same time being able thereafter to hold the sleeve 171 inside this reservoir 10, in spite of the return action of the spring 189.

Figure 38:
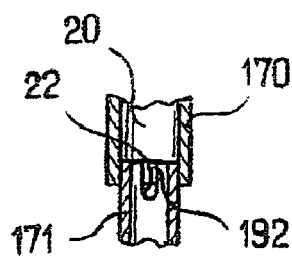

FIG. 38 depicts the possibility of producing the withdrawing tube with a lateral orifice 22 formed by a slot 192. This slot defines an opening the dimension of which can vary according to the relative position of the upper part of the withdrawing tube and of the sleeve 171, the latter in the example illustrated being produced with the slot 192.

The sleeve 171 is, for example, designed to screw into the upper part 170 so as to allow the user or the factory to adjust the cross section of the lateral orifice 22, so as to control, for example, the flow rate of powder sucked in.

Figure 39:
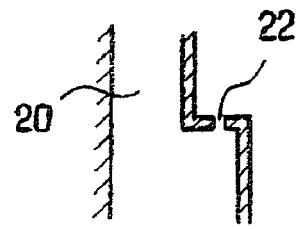

As appropriate, the lateral orifice 22 may be produced differently, for example on a shoulder of the withdrawing tube 20, as illustrated in FIG. 39.

Throughout the description, the expression "comprising a" is to be understood as meaning the same as "comprising at least one", unless specified to the contrary.

The invention claimed is:

1. Micro-abrasion device comprising:
   a base station;
   a handpiece configured to spray a powder onto skin;
   a flexible supply pipe configured to supply powder from the base station to the handpiece;
   a flexible return pipe configured to return powder from the handpiece to the base station; and
   a removable cartridge configured to be fitted onto the base station and removed therefrom, the cartridge comprising:
   a first reservoir containing a powder to be supplied to the handpiece via said flexible supply pipe, and
   a second reservoir configured to collect powder returning from the handpiece via said flexible return pipe.

2. A device according to claim 1, wherein the first and second reservoirs are connected together non-removably within the cartridge.

3. A device according to claim 1, characterized in that the first and second reservoirs form two compartments within a body of the cartridge.

4. A device according to claim 1, wherein the first and the second reservoirs are contiguous within the cartridge.

5. A device according to claim 4, wherein the first and second reservoirs include a common wall.

6. A device according to claim 1, wherein the first reservoir includes a longitudinal axis and wherein a section of the first reservoir transverse to the longitudinal axis narrows toward a bottom of the first reservoir.

7. A device according to claim 1, wherein the first reservoir comprises a tube including an open upper end.

8. A device according to claim 7, wherein the tube comprises a lateral orifice allowing the powder to be supplied to the handpiece to enter the tube.

9. A device according to claim 1, wherein the first reservoir comprises an air intake on a side wall of the first reservoir.

10. A device according to claim 1, wherein the cartridge comprises a puncturable seal configured to close off a connection endpiece configured to connect the first reservoir to the base station.

11. A device according to claim 10, wherein the base station comprises a housing configured to accept the cartridge and wherein the housing is configured to prevent the cartridge from being inserted in the housing in anything other than a determined position.

12. A device according to claim 1, wherein the cartridge comprises a moulded plastic body and a closure cap attached to the body.

13. A device according to claim 1, wherein the base station comprises a housing configured to accommodate the cartridge and wherein the housing is provided with a sealing piece made of elastomer.

14. A device according to claim 1, wherein the cartridge comprises endpieces in communication with the first and second reservoirs and wherein the sealing piece is configured to press in a sealed manner against the endpieces of the cartridge.

15. A device according to claim 1, wherein the powder is based on cereal flour.

16. A device according to claim 14, wherein the endpieces are made by molding as a single piece with a body of the cartridge.

17. A device according to claim 1, wherein the base station comprises a vacuum pump.

18. A device according to claim 1, wherein the base station comprises a first housing configured to accommodate the cartridge and around the first housing a second housing of annular shape configured to house the flexible supply and return pipes was inserted therefore connecting the handpiece to the base station.

19. A device according to claim 18, further comprising a hinged lid configured to close the first housing.

20. A device according to claim 18, further comprising a boss provided with the first housing, the boss comprising a depression configured to accept the handpiece when not in use.

21. A device according to claim 20, wherein the boss comprises third and forth housings configured to accommodate handpieces configured to be fitted to a body of the handpiece.

* * * * *